United States Patent
Götz et al.

(10) Patent No.: US 7,034,181 B1
(45) Date of Patent: *Apr. 25, 2006

(54) METHOD FOR PRODUCING O-CHLOROMETHYL BENZOIC ACID CHLORIDES

(75) Inventors: Roland Götz, Neulussheim (DE); Norbert Götz, Worms (DE); Michael Keil, Freinsheim (DE); Bernd Wolf, Fussgönheim (DE); Adrian Steinmetz, Mannheim (DE); Armin Stamm, Mainz (DE); Jochem Henkelmann, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/130,821

(22) PCT Filed: Nov. 27, 2000

(86) PCT No.: PCT/EP00/11817

§ 371 (c)(1),
(2), (4) Date: May 23, 2002

(87) PCT Pub. No.: WO01/42185

PCT Pub. Date: Jun. 14, 2001

(30) Foreign Application Priority Data

Dec. 7, 1999 (DE) .............................. 199 58 757
Feb. 19, 2000 (DE) .............................. 100 07 694

(51) Int. Cl.
*C07C 51/58* (2006.01)
(52) U.S. Cl. ...................................... 562/862; 562/861
(58) Field of Classification Search ................ 562/840, 562/856, 857, 861, 864
See application file for complete search history.

(56) References Cited

U.S. PATENT DOCUMENTS

| 5,130,478 A | * | 7/1992 | Gauthier et al. ............. 562/857 |
| 6,222,060 B1 | * | 4/2001 | Kim et al. ..................... 560/14 |
| 6,727,385 B1 | * | 4/2004 | Gotz et al. ................... 562/853 |

FOREIGN PATENT DOCUMENTS

| EP | 0 460 575 | | 12/1991 |
| EP | 0 463 488 | | 1/1992 |
| EP | 0 676 389 | | 10/1995 |
| EP | 676 389 | | 10/1995 |
| WO | WO 95/18789 | | 7/1995 |
| WO | WO 95/21154 | | 8/1995 |
| WO | 97/12854 | | 4/1997 |
| WO | WO 97/12854 | | 4/1997 |
| WO | WO 97/15552 | | 5/1997 |
| WO | 99/16743 | | 4/1999 |
| WO | WO 99/16743 | | 4/1999 |
| WO | 200142183 | * | 6/2001 |

* cited by examiner

*Primary Examiner*—Johann Richter
*Assistant Examiner*—Karl Puttlitz
(74) *Attorney, Agent, or Firm*—Novak Druce & Quigg, LLP

(57) ABSTRACT

The invention relates to a method for producing o-chloromethyl benzoic acid chlorides of formula (I), in which $R^1$ to $R^4$ can be the same or different and represent hydrogen $C_1$–$C_4$ alkyl, halogen or trifluoromethyl, by reaction benzo condensed lactones of formula (II), in which $R^1$ to $R^4$ have the above-mentioned meaning, with thionyl chloride. The inventive method is characterized in that the reaction is carried out in the presence of catalytic quantities of a Lewis acid and in the presence of catalytic quantities of a phosphine derivative.

9 Claims, No Drawings

METHOD FOR PRODUCING O-CHLOROMETHYL BENZOIC ACID CHLORIDES

TECHNICAL FIELD

The present invention relates to a process for preparing o-chloromethylbenzoyl chlorides of the formula I

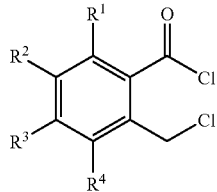

in which $R^1$ to $R^4$ can be identical or different and are hydrogen, $C_1$–$C_4$-alkyl, halogen or trifluoromethyl, by reacting benzo-fused lactones of the formula II

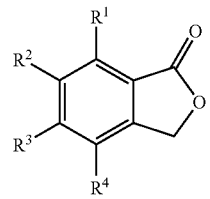

in which $R^1$ to $R^4$ are as defined above with thionyl chloride.

BACKGROUND ART o-Chloromethyl-substituted benzoyl chlorides are important intermediates for preparing, for example, pesticidally active compounds as described in the patents EP-A 460 575, EP-A 463 488, WO-A 95/18789, WO-A 95/21154 and WO-A 97/15552.

o-Chloromethyl-substituted benzoyl chlorides can be prepared, for example, by reacting benzo-fused lactones with thionyl chloride or phosgene. If thionyl chloride is used, the apparatus is simplified and the safety precautions reduced.

EP-A 676 389 describes the preparation of o-chloromethylbenzoyl chlorides from benzo-fused lactones using thionyl chloride in the presence of a nitrogen compound. To achieve a satisfactory conversion, reaction temperatures of 160–170° C. are required, at which thionyl chloride is already partially decomposed, resulting in the formation of troublesome byproducts. Furthermore, the addition of gaseous hydrochloric acid is required. Finally, in some cases the yields are considerably less than 90%.

WO 97/12854 describes a process for preparing o-chloromethylbenzoyl chlorides by phosgenation of benzo-fused lactones in the presence of a triarylphosphine oxide catalyst at 170° C. In contrast to thionyl chloride, phosgene is thermally stable under these conditions; however, the handling of phosgene and its holdup in the condenser at the high temperatures involved are made more difficult by increased safety precautions. Furthermore, under these conditions the reaction product is under high thermal stress, which may result in its partial decomposition.

In WO-A 99/16743, the reaction with thionyl chloride is carried out in the presence of a quaternary ammonium salt and a Lewis acid at 90–100° C. However, quaternary ammonium salts are problematic from an environmental point of view and have the following technical disadvantages: sublimation may result in parts of the plant being blocked. Furthermore, the salts are hygroscopic, which may lead to water being introduced, resulting in more chlorinating agent being consumed. Finally, the ammonium salts interfere with the distillative purification of the o-chloromethylbenzoyl chlorides.

DISCLOSURE OF INVENTION

It is an object of the present invention to provide an economical process suitable for industrial implementation for preparing o-chloromethylbenzoyl chlorides which does not have the above-mentioned disadvantages and still affords high yields.

We have found that this object is achieved by the process mentioned at the outset, which comprises carrying out the reaction in the presence of catalytic amounts of a Lewis acid and catalytic amounts of a phosphine derivative of the formula III

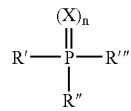

in which R' to R''' can be identical or different and are $C_1$–$C_{10}$-alkyl or unsubstituted or $C_1$–$C_4$-alkyl-substituted phenyl and the index n is 0 or 1. X is oxygen or two singly attached chlorine atoms.

MODE(S) FOR CARRYING OUT THE INVENTION

The starting materials used are benzo-fused lactones (phthalides) of the formula II

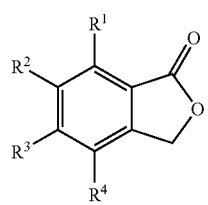

in which $R^1$ to $R^4$ can be identical or different and are hydrogen (H), $C_1$–$C_4$-alkyl, halogen (fluorine, chlorine, bromine or iodine) or trifluoromethyl. Preference is given to using unsubstituted phthalide.

One of the catalysts used is a phosphine or phosphine oxide of the formula III

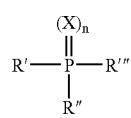

in which R' to R''' can be identical or different and are $C_1$–$C_{10}$-alkyl or unsubstituted or $C_1$–$C_4$-alkyl-substituted phenyl. The index n is 0 or 1 and X is oxygen or two singly attached chlorine atoms. Preference is given to unsubstituted triphenylphosphine oxide.

The use of trialkylphosphine oxides which are liquid at room temperature has, in particular, technical advantages (the handling of solids is dispensed with, discharge of the distillation residue during purification is easier) and is therefore likewise preferred. The tri($C_6$–$C_8$-alkyl)phosphine oxides obtainable under the tradename Cyanex® (for example Cyanex® 923 from Cyanamid) are, for example, suitable here. Liquid trialkylphosphine oxides in combination with Lewis acids such as boric acid, tri($C_1$–$C_4$-alkyl) borate and boron trifluoride adducts have been found to be particularly useful.

The phosphine derivative is generally added in amounts of from 0.1 to 20 mol %, based on the amount of benzo-fused lactone used, and is preferably added in amounts of from 0.5 to 10 mol %.

Suitable Lewis acids are, in particular, boron compounds such as $BF_3$, $BCl_3$ (or their complexes with oxygen compounds, sulfur compounds or nitrogen compounds), boronic acids—e.g. arylboronic acids (especially phenylboronic acid), their $C_1$–$C_4$-alkyl esters and also $C_1$–$C_6$-alkylboronic acids and their $C_1C_4$-alkyl esters—, cyclic boric esters (especially tris($C_1$–$C_4$-alkoxy)boroxin), boric acid tri ($C_1$–$C_4$-alkyl) esters, boric anhydride, borate (especially sodium borate/borax), and boric acid ($H_3BO_3$) itself. Also suitable are heterogeneous, Lewis-acidic aluminosilicates of the zeolite type.

Preference is given to $BF_3$ and its complexes with ether (in particular diethyl ether), water (dihydrate), alcohol (in particular methanol), sulfide (in particular dimethyl sulfide) and amine (in particular ethylamine). Particularly suitable are $BF_3$ etherate and $BF_3$ dihydrate.

The Lewis acids used are particularly preferably boric acid, boric acid tri($C_1$–$C_4$-alkyl) esters or cyclic boric esters. Examples of suitable cyclic boric esters include trimethoxyboroxin and triethanolamine borate. Such processes give excellent yields and have the advantage that the reaction mixtures are free from fluoride ions. Thus, compared to the analog reaction where $BF_3$ derivatives are used as Lewis acid, the entire apparatus is simplified.

The Lewis acid is added in amounts of from 0.1 to 20 mol %, based on the amount of benzo-fused lactone used, and is preferably added in amounts of from 0.5 to 5 mol %.

It may furthermore be advantageous to use heterogeneous Lewis-acidic catalysts, such as, for example, zeolites of the faujasite type in which some or all exchangeable cations have been replaced by protons. A heterogeneously catalyzed reaction has the advantage that it can be carried out in a fixed bed. The heterogeneous catalyst is employed in amounts of from 0.01 to 10% by weight and preferably in amounts of from 0.1 to 1% by weight, based on the amount of benzo-fused lactone used.

Based on the phthalide II, in general from 1 to 1.5 equivalents of thionyl chloride are used.

The thionyl chloride can be initially charged together with the other reactants (batch operation) or be metered in in the course of the reaction, preferably over a period of 1–8 hours, (semi-batch operation). It is furthermore possible to carry out the reaction continuously.

If desired, gaseous hydrogen chloride can be introduced to accelerate ring opening. However, the introduction of hydrogen chloride during the synthesis is preferably dispensed with.

In the case of the boron halides, the reaction temperature is generally 80–140° C. and preferably 90–110° C. If boric acid or tri($C_1$–$C_4$-alkyl) borates are used, the reaction temperature is generally 100–180° C. and preferably 110–140° C.

The process is preferably carried out in the absence of a solvent However, it is possible to add a solvent which is inert to thionyl chloride. Inert solvents are, for example, aromatic hydrocarbons, such as toluene, o-, m- or p-xylene or mixtures thereof, chlorinated aromatic hydrocarbons, such as chlorobenzene or dichlorobenzenes, or cyclic carbonates, such as ethylene carbonate or propylene carbonate. It is furthermore possible to use thionyl chloride itself as solvent which can be removed distillatively at the end of the reaction and be recycled into the process.

The reaction is generally carried out at atmospheric pressure or at a pressure of from 1 to 10 bar. The examples below serve to illustrate the process in more detail.

PROCESS EXAMPLES

General Procedure for Preparing O-chloromethylbenzoyl chloride

In a stirred apparatus consisting of a 1.6 l double-jacketed reactor with an attached battery of high-efficiency condensers, in each case x mol of phthalide were initially charged together with the catalyst system in question. 1.3 equivalents of thionyl chloride, based on the phthalide, were either initially charged together with the other components or added dropwise over a period of from 1 to 8 hours. The mixture was then stirred at the reaction temperature for another 1 to 15 hours. The content of the product of value of the crude mixture was determined by GC. In selected examples, the product was isolated at 0.5 mbar and 75–85° C. by fractional distillation.

Example 1

134 g (1 mol) of phthalide, 1.9 g (0.03 mol, 3 mol %) of boric acid and 8.5 g (0.03 mol, 3 mol %) of triphenylphosphine oxide were initially charged in a stirred vessel and heated to 130° C. Over a period of 3 hours, 155 g (1.3 mol) of thionyl chloride were added dropwise to this melt. The mixture was subsequently stirred at 130° C. for another 5 hours. The reaction discharge (183 g) contained 97 GC-area % of o-chloromethylbenzoyl chloride.

Example 2

670 g (5 mol) of phthalide, 26 g (0.25 mol, 5 mol %) of trimethyl borate and 70.5 g (0.25 mol, 5 mol %) of triphenylphosphine oxide were initially charged in a stirred vessel and heated to 130° C. Over a period of 5 hours, 774 g (6.5 mol) of thionyl chloride were added dropwise to this melt. The mixture was subsequently stirred at 130° C. for another 5 hours. Distillation of the reaction discharge gave 940 g (99.4% yield) of o-chloromethylbenzoyl chloride with a purity of 98% (GC).

Example 3

268 g (2 mol) of phthalide, 10.4 g (0.1 mol, 5 mol %) of trimethyl borate and 33.4 g (0.096 mol, 4.8 mol %) of Cyanex® 923 and 310 g (2.6 mol) of thionyl chloride were initially charged in a stirred vessel and heated to 120° C. The mixture was subsequently stirred at 120° C. for another 4 hours. The reaction discharge contained 84 GC-area % of o-chloromethylbenzoyl chloride and 9% of unreacted phthalide.

Example 4

268 g (2 mol) of phthalide, 14.8 g (0.1 mol, 5 mol %) of boron trifluoride etherate and 33.4 g (0.096 mol, 4.8 mol %) of Cyanex® 923 and 310 g (2.6 mol) of thionyl chloride were initially charged in a stirred vessel and heated to 100° C. The mixture was subsequently stirred at 100° C. for another 15 hours. The reaction discharge contained 93 GC-area % of o-chloromethylbenzoyl chloride and 2.8% of unreacted phthalide. Following distillation, the product of value was isolated in a yield of 89%.

Example 5

268 g (2 mol) of phthalide, 17.8 g (0.12 mol, 6 mol %) of boron trifluoride etherate and 40 g (0.12 mol, 6 mol %) of triphenylphosphine dichloride and 310 g (2.6 mol) of thionyl chloride were initially charged in a stirred vessel and heated to 100° C. The mixture was subsequently stirred at 100° C. for another 15 hours. The reaction discharge contained 92 GC-area % of o-chloromethylbenzoyl chloride and 5% of unreacted phthalide.

Example 6

134 g (1 mol) of phthalide, 7.9 g (0.05 mol, 5 mol %) of boron trifluoride dihydrate and 16.7 g (0.048 mol, 4.8 mol %) of Cyanex® 923 and 155 g (1.3 mol) of thionyl chloride were initially charged in a stirred vessel and heated to 100° C. The mixture was subsequently stirred at 100° C. for another 7 hours. The reaction discharge contained 83 GC-area % of o-chloromethylbenzoyl chloride and 7% of unreacted phthalide.

Example 7

268 g (2 mol) of phthalide, 10.4 g (0.1 mol, 5 mol %) of trimethyl borate and 26.3 g (0.1 mol, 5 mol %) of triphenylphosphine were initially charged at 130° C. 310 g (2.6 mol) of thionyl chloride were added dropwise to this mixture over a period of 5 hours. The mixture was subsequently stirred at 130° C. for another 5 hours. The reaction discharge contained 98 GC-area % of o-chloromethylbenzoyl chloride.

Example 8

An initial charge of 13.4 g (0.1 mol) of phthalide, 1.08 g (5 mol %) of di(isopropyl) phenylboronate and 1.4 g (5 mol %) of triphenylphosphine oxide was admixed dropwise with 15.5 g (0.13 mol) of thionyl chloride. The mixture was subsequently stirred at 130° C. for 10 hours. The reaction discharge contained 86 GC-area % of o-chloromethylbenzoyl chloride.

Example 9

A mixture of 13.4 g (0.1 mol) of phthalide, 15.5 g (0.13 mol) of thionyl chloride, 0.82 g (5 mol %) of trimethoxyboroxin and 1.4 g (5 mol %) of triphenylphosphine oxide was stirred at 130° C. for 10 hours. The reaction discharge contained 95.4 GC-area % of o-chloromethylbenzoyl chloride.

We claim:

1. A process for preparing o-chloromethylbenzoyl chlorides of the formula I

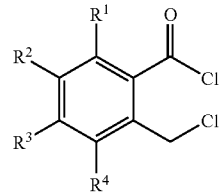

in which $R^1$ to $R^4$ are identical or different and are hydrogen, $C_1$–$C_4$-alkyl, halogen or trifluoromethyl, by reacting benzofused lactones of the formula II

II in which $R^1$ to $R^4$ are as defined above with thionyl chloride, which comprises carrying out the reaction in the presence of catalytic amounts of a Lewis acid and catalytic amounts of a phosphine derivative of the formula III

III $$R'\!-\!\underset{R''}{\overset{(X)_n}{\underset{|}{P}}}\!-\!R'''$$

in which R' to R''' are identical or different and are $C_1$–$C_{10}$-alkyl or unsubstituted or $C_1$–$C_4$-alkyl-substituted phenyl, the index n is 0 or 1 and X is oxygen or two singly attached chlorine atoms, wherein the Lewis acid is a boron compound.

2. A process as claimed in claim 1, wherein the Lewis acid used is boric acid.

3. A process as claimed in claim 1, wherein the Lewis acid used is boron trifluoride or boron trichloride in coordinate form.

4. A process as claimed in claim 1, wherein the Lewis acid used is a cyclic borate or a tri-$C_1$–$C_4$-alkyl borate.

5. A process as claimed in claim 1, wherein the Lewis acid used is a boronic acid, a boric anhydride or a borate.

6. A process as claimed in claim 1, wherein the Lewis acid is used in a concentration of from 0.1 to 20 mol %, based on the lactone II.

7. A process as claimed in claim 1, wherein the phosphine derivative used is triphenylphosphine oxide.

8. A process as claimed in claim 1, wherein the phosphine derivative used is a trialkylphosphine oxide which is liquid at room temperature.

9. A process as claimed in claim 1, wherein from 0.1 to 20 mol % of the phosphine derivative, based on the lactone II, are used.

* * * * *